(12) United States Patent
De Leon et al.

(10) Patent No.: US 8,128,907 B2
(45) Date of Patent: *Mar. 6, 2012

(54) CSF BIOMARKER DILUTION FACTOR CORRECTIONS BY MRI IMAGING AND ALGORITHM

(75) Inventors: Mony De Leon, New York, NY (US); Henry Rusinek, Great Neck, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/799,484

(22) Filed: Apr. 26, 2010

(65) Prior Publication Data

US 2010/0228115 A1    Sep. 9, 2010

Related U.S. Application Data

(63) Continuation of application No. 10/508,065, filed on Jun. 7, 2005, now Pat. No. 7,736,623.

(60) Provisional application No. 60/365,941, filed on Mar. 20, 2002.

(51) Int. Cl.
*A61B 5/055*    (2006.01)
*G01N 33/53*    (2006.01)
*G01N 33/542*    (2006.01)
*G01N 33/566*    (2006.01)
*C12Q 1/00*    (2006.01)

(52) U.S. Cl. ............... 424/9.3; 435/7.1; 435/4; 435/7.9; 435/7.92; 436/501

(58) Field of Classification Search ........................ None
See application file for complete search history.

(56) References Cited

U.S. PATENT DOCUMENTS 7,736,623 B2 *    6/2010    De Leon et al. ............... 424/9.3

OTHER PUBLICATIONS

M. Yoshihara et al., Differential Diagnosis of NPH and Brain Assessed by Measurement of Intracranial and Ventricular CSF Volume with 3D FASE MRI, Acta Neurochi (1998) 71:371-374.
Raquel E. Gur et al., Clinical Subtypes of Schizophrenia: Differences in Brain and CSF Volume, Am. J. Psychiatry, 115:3, Mar. 1994.
Fox and Freeborough, Brain Atrophy Progression Measured from Registered Serial MRI: Validation and Application to Alzheimer's Disease, JMRI., 1069-1075, Nov./Dec. 1997.
Bedell and Narayana, Volunetric Analysis of White Matter, Gray Matter, and CSF Using Fractional Volume Analysis, MRM 39:961-969 (1998).
Clifford R. Jack, Jr., MD, Brain and Cerebrospinal Fluid Volume: Measurement with MR Imaging, Radiology, 1991, 178: 22-24.
John A. Malko et al., MR Measurement of Intracranial CSF Volume in 41 Elderly Normal Volunteers, AJNR: Mar. 12/Apr. 1991.
J.B. Chawluk, Quantifying Intracranial CSF Volume Using MRI, Letter to the Editor, Journal of Nuclear Medicine, vol. 29:132-133, No. 1, Jan. 1998.
Mony J. De Leon et al., Alzheimer's Disease: Longitudinal CT Studies of Ventricular Change, AJNR: 10:371-376, Mar./Apr. 1998.
Henry Rusinek, PhD et al. Alzheimer Disease: Measuring Loss of Cerebral Gray Matter with MR Imaging, Radiology 1991; 178: 109-114.
M.J. de Leon et al., Longitudinal cerebrospinal fluid tau load increases in mild cognitive impairment, Neuroscience Letters 333 (2002) 183-186.
M.J. de Leon et al., Frequency of Hippocampal Formation Atrophy in Normal Aging and Alzheimer's Disease, Neurobiology of Aging, vol. 18, No. 1, pp. 1-11. 1997.
M.J. De Leon et al., The Radiologic Prediction of Alzheimer Disease; the Atrophic Hippocampal Formation, AJNR 14:897-906, Jul./Aug. 1993.
Ajax E. George, et al., Ventricular Volume and Cognitive Deficit: A Computed Tomographic Study, Radiology 1983; 149:493-498.
Harris et al., User-Friendly Method for Rapid Brain and CSF Volume Calculation Using Transaxial MRI Images, Psychiatry Research: Neuroimaging 1991, 40:61-68, Elsevier.
Peter A. Freeborough et al., Interactive algorithms for the segmentation and quantitation of 3-D MRI brain scans, Computer Methods and Programs in Biomedicine 53 (1997) 15-25 Elsevier.
Tsui et al., Analyzing multi-modality tomographic images and associated regions of interest with MIDAS,: Proceedings of the SPIE, SPIE, Bellingham, VA, 2001; 4332 (pt 1-3): 1725-1734.

* cited by examiner

*Primary Examiner* — Olga N Chernyshev
(74) *Attorney, Agent, or Firm* — Klauber & Jackson LLC

(57) ABSTRACT

A method is disclosed for providing a correcting factor for the dilution of measurements of at least one biomarker in cerebrospinal fluid (CSF). The method comprises providing semi-automated measurements of the ventricular system by MRI scans using quantitative anatomical protocols, determining a measurement of biomarker levels in CSF that has been extracted, correcting the measurement of the level of said at least one biomarker'according to the ventricular size, and providing a corrected result of the measurement determined in step (b), said corrected result accounting for concentration dilution due to the change in ventricular size. The method is particularly suited for the measurement of all biomarkers found in the CSF, such as those associated with mild cognitive impairment (MCI) and Alzheimer's Disease.

13 Claims, 2 Drawing Sheets

FIG. 1

START (a) providing semi-automated measurements of the ventricular system by MRI scans using quantitative anatomical protocols;

(b) determining a measurement of biomarker levels in CSF that has been extracted;

(c) correcting the measurement of the level of said at least one biomarker according to ventricular size; and (d) providing a corrected result for the measurement in step (b) that has accounted for concentration dilution in the CSF due to the change in ventricular size.

END

FIG. 2

START (a) co-registration of a baseline scan and a follow-up scan of magnetic resonance (MR) images;

(b) obtaining semi-automated measurements by constructing a border region B and two interior regions $I_{bas}$, $I_{fol}$ for the entire brain and for each predetermined anatomical subvolume of interest;

(c) computing of signal loss and volume loss of the brain to derive a volume of CSF in the brain, and (d) providing an output of a correction factor for correcting a tested level of at least one biomarker in the CSF.

END

CSF BIOMARKER DILUTION FACTOR CORRECTIONS BY MRI IMAGING AND ALGORITHM

CROSS REFERENCE TO RELATED APPLICATIONS

This present application is a continuation of U.S. Ser. No. 10/508,065 filed Jun. 7, 2005 now U.S. Pat. No. 7,736,623, which claims priority of co-pending PCT Application No. PCT/US03/10110 filed Mar. 20, 2003, which in turn, claims priority from U.S. Provisional Application No. 60/365,941, filed Mar. 20, 2002. Applicants claim the benefits of 35 U.S.C. §120 as to the PCT application and priority under 35 U.S.C. §119 as to the provisional application, and the entire disclosures of both applications are incorporated herein by reference in their entireties.

BACKGROUND OF THE INVENTION

1. Field of the Invention

The present invention relates to the analysis of biomarkers in cerebrospinal fluid (CSF). More particularly, the present invention relates to (1) discovering the importance of correcting CSF biomarker levels for their dilution in CSF and (2) correcting CSF measures for their dilution using a semi-automated procedure for determining CSF volumes in patients with variable and disease-related increases in CSF volume. This invention is important for diagnosing and monitoring the course of Alzheimer's disease, but the scope of the invention reaches far beyond diagnosing and monitoring of Alzheimer's disease. For example, the invention can be applied to monitor other disorders, such as vascular dementia, boxer's syndrome, multiple sclerosis, amyotrophic lateral sclerosis (ALS), and stroke, just to name a few.

2. Description of the Related Art

Cerebrospinal Fluid (CSF) is a liquid that fills the ventricles of the brain and the spaces between arachnoid matter and pia matter of the brain and spinal cord. As the CSF is in contact with the brain, it has been known for some time that Alzheimer's Disease and other dementia-related illnesses can be diagnosed (and the progression of the illness monitored) by analyzing biomarkers in the CSF.

In addition, as more progress is made in the development of drugs that inhibit/slow down the progression of Alzheimer's Disease, analyzing the biomarkers can be used to evaluate the effectiveness of a drug on a particular patient, or group of patients.

However, heretofore, the process for analyzing biomarkers in CSF has been slow, cost prohibitive, and has not always provided accurate results. In fact, the sometimes inaccurate results of the prior art can hinder research and development of effective drugs, as well as increase the likelihood that a proper diagnosis of a particular illness may not be made in a timely fashion, or not at all for that matter.

One of the biomarkers of interest has been for some time, the tau protein and related forms thereof. In general, tau proteins are constituents of the neuronal axons. Under conditions of neuronal and synaptic degeneration, as is found with the progression of Alzheimer's Disease, the amount of tau protein in the CSF increases. Surgical research studies for non-Alzheimer related reasons have shown that the ventricular derived CSF concentration of tau (a protein found in all people) is two-fold higher than in the lumbar spinal tap derived CSF which is used for diagnostic purposes.

Lumbar spine derived CSF tau levels are elevated in the early stages of Alzheimer's Disease, perhaps before dementia is even noticeable or detectable in a clinical setting. However, longitudinal studies have reported that both in cases of mild cognitive impairment (MCI), as well as Alzheimer's, tau levels, as well as CSF amyloid beta 1-42 (Aβ42) levels, a marker for the fibrillar amyloid that is deposited in Alzheimer's disease in the form of senile plaques, do not significantly change over time in deteriorating patients.

The present inventors submit that the surprising result regarding the lack of a significant change in the above-mentioned biomarkers is likely the result of a disease-related increase in the size of the brain's CSF compartment, a compensatory response to the loss of brain tissue. In other words, the amount of CSF increases to compensate for reduced brain volume thus diluting the absolute amount of the biomarker thus causing the afore-mentioned biomarkers in the CSF to remain at similar levels, masking the amount of neuronal deterioration that has taken place when comparing a series of test results taken over time, or compared against predetermined concentration values.

Heretofore, neuroimaging methods have not been used to correct the diluted CSF biomarker. The prior art methods using MRI scans to calculate the CSF compartment heretofore have been cost prohibitive because of the need for highly trained persons to spend sometimes as much as several hours to calculate CSF volume for a single patient by methods that require manual identification and dissection of areas of the brain, with the ventricular size and other CSF containing structures being determined by the number of pixels counted in each of the areas identified. In particular, defining the anatomical boundaries of the ventricular system from MRI scans is complex and time consuming. The MRI scans can number as many as fifty or more "slices" of the ventricle being scanned, thus making the calculations a rather tedious procedure, and subject to error even by highly trained personnel. The prior art has had attempts to provide a semi-automated program to measure the whole brain CSF, but there was absolutely no disclosure, suggestion or motivation that the determination of ventricular size could be used to correct biomarkers in CSF volumes. Accordingly, a more reliable and less expensive way to perform such testing is needed in the art.

SUMMARY OF THE INVENTION

The present invention discloses a novel method for correcting biomarker dilution in ventricular CSF that greatly reduces the time needed to make the corrections, thus permitting relatively inexpensive and accurate diagnosis and monitoring of biomarkers that heretofore were previously cost-prohibitive to be used as a routine test. The application of the invention can be to correct any biomarker found in CSF, and not just the markers associated with MCI and Alzheimer's Disease.

The present invention permits a fast and accurate method for detection of ventricular size so as to adjust the level of biomarkers according to the CSF volume that reduces the time to make the correction to a matter of minutes, and does not require highly trained specialists in brain anatomy to study the scans. The costs to perform the correction allow for a fast and inexpensive way (so as to be covered by health insurance) to test for cases of MCI, Alzheimer's Disease, both for those who show signs of such illnesses, as well as for those who do not, by combining MRI and CSF markers to improve the sensitivity and specificity for the prediction of cognitive decline.

The benefits of the present invention include the ability to detect a problem and permit the prescription of drugs to slow/inhibit the progression of some of the aforementioned brain disorders before the patient's illness has advanced to a stage where it has a severe impact.

The present invention provides a significant advance in the ability to rapidly process ventricular volume of the brain.

The present invention allows the correction of the biomarker levels in CSF by using the MRI or CT scans, much more quickly than known heretofore, so as to evaluate disorders which are detectable through identification and quantification of biomarkers in the CSF. The detection of many of the disorders that are detectable by the present invention was impractical according to prior art methods.

According to one application of the present invention, it is proposed that progressive hippocampal and entorhinal cortex (EC) atrophy, early sites of Alzheimer pathology, can be best predicted by elevated CSF P-tau231 levels that are corrected according to the improved diagnostic accuracy of the present invention.

It is also proposed that progressive neocortical atrophy can best be predicted by reductions in CSF Aβ40 and Aβ42 levels that are corrected according to the improved diagnostic accuracy of the present invention. Again, it should be noted that while the present invention has a particular significance in correcting specific biomarkers in CSF for detecting Alzheimer's and MCI, the present invention can be used for any brain originating or other biomarker found in CSF in which its concentration would be affected by a change in ventricular size.

It is also proposed that the present invention is not limited to a method for biomarker correction based on an adjusted CSF volume according to ventricular size, but can be use to track atrophy in other parts of the brain. It is proposed that blood from a patient can be tested for the presence of biomarkers in conjunction with the levels of CSF corrected biomarkers in the CSF to obtain a more accurate correlate of blood values and possibly improve a non-invasive diagnostic understanding of a patient's illness, or the progression thereof.

According to a first embodiment of the present invention, a method for correcting measurements of at least one biomarker in cerebtospinal fluid (CSF) comprises:
(a) providing semi-automated measurements of the ventricular system by MRI scans using quantitative anatomical protocols;
(b) determining a measurement of biomarker levels in CSF that has been extracted;
(c) correcting the measurement of the level of said at least one biomarker according to the ventricular size; and
(d) providing a corrected result of the measurement determined in step (b), said corrected result accounting for concentration dilution due to the increase in ventricular size (which can be caused by the decrease in the size of the damaged brain). It is known from using MRI that the hippocampus and EC are affected earliest in the course of Alzheimer's disease. Thus, said correlated CSF corrected results in combination with MRI improve the diagnostic sensitivity and specificity.

The change that can be measured is the change in ventricular size at one time point or over time, and is used to adjust the amount of biomarker measured in the CSF. The adjusted amount of a particular biomarker level in the CSF is due to the correlated MRI scan of the brain and measurement of the ventricular volume. The MRI corrected CSF biomarker can then be used to assess cross sectional deviations from reference norms and longitudinal change.

In addition to measuring the ventricular size from MRI scans, it is possible using the semi-automated procedures herein that there can be a measurement of the change in measurement of other regions of the brain, including the EC, hippocampus, and other potentially vulnerable regions of the brain. The research shows that the hippocampus (de Leon, M. J., Golomb, J., George, et al (1993), The radiologic prediction of Alzheimer's disease: The atrophic hippocampal formation, American Journal of Neuroradiology 14: 897-906. and entorhinal cortex (de Leon, M. J., Convit, A., et al (2001), Prediction of cognitive decline in normal elderly subjects with 2-[18F]fluoro-2-deoxy-D-glucose/positron-emission tomography (FDG/PET), Proc. Natl. Acad. Sci. USA, 98, 10966-10971) are predictors of progressive memory loss and cognitive decline in Alzheimer's Disease.

These useful measurements in the early diagnosis and prediction of future Alzheimer's disease are further improved using the CSF corrected biomarker tau.

In an embodiment specifically directed to correcting certain specific biomarkers for Alzheimer's Disease and MCI, just to name a few of the many possibilities, the above-mentioned steps (c) and (d) would be modified as follows:
(c) correcting the measured level of tau and related proteins (P-tau231) and fragment of amyloid beta found in the CSF by an algorithm that analyzes the measurements from the MRI scans of ventricular size; and
(d) providing a corrected result that has accounted for concentration dilution in the CSF due to the increase in ventricular size (caused by the decrease in the size of the brain).

The present invention can be particularly valuable when used to correct biomarker levels for the aforementioned illnesses because neuropathology studies show that damage to the hippocampus and entorhinal cortex, the brain's major memory processing center, occurs early in the course of Alzheimer's Disease. Thus more biomarker proteins are sequestered in the CSF compartment of the brain. Thus, an accurate measurement of increased ventricular size rapidly and inexpensively provides a significant improvement over the prior art.

The determining of CSF biomarker levels in step (b) may include a time limitation (plus or minus a predetermined amount of time) before or after the MRI for a level of at least one predetermined biomarker.

According to yet another embodiment of the present invention, Aβ42 levels in CSF are corrected by:
(a) MRI scans using quantitative anatomical protocols to provide measurements of the ventricular system, and that may optionally include measuring the EC, hippocampus, and vulnerable neocortical regions of the brain;
(b) testing CSF that has been extracted plus or minus a predetermined time period before or after the MRI for CSF Aβ42 levels;
(c) correcting the measurement of the level of Aβ42 in the CSF by an algorithm that analyzes the measurements from the MRI scans of at least the ventricular size; and
(d) providing a corrected result that has accounted for concentration dilution due to the increase in ventricular size.

According to still another embodiment of the invention, both P-tau 231 and Aβ42 levels are corrected by: (a) MRI scans using quantitative anatomical protocols to provide measurements of the ventricular system; (b) testing CSF that has been extracted within a predetermined amount of time before or after the MRI for P-tau231 and CSF Aβ42 levels; (c) correcting the measurement of the level of Aβ42 in the CSF by an algorithm that analyzes the measurements from the MRI scans of at least the ventricular system; and (d) providing a corrected result that has accounted for concentration dilution due to the increase in ventricular size (caused by the decrease in the brain tissue volume).

The algorithm factors in the change in measurements of the areas of the brain are based on the underlying hypothesis of the present inventor: In the early stages of Alzheimer's the brain, particularly the hippocampus, decreases in size, and the volume of the ventricle increases proportionally. The amount of CSF fluid increases as the brain attempts to maintain it's structural integrity within the bony calvarium.

Thus, with the decrease in hippocampal and EC sizes being one early indicator consistent with Alzheimer's Disease, the brain increases the ventricular CSF volume. Accordingly, with each progressive stage of Alzheimer's (or other forms of dementia previously mentioned) the ventricular CSF volume increases and progressively dilutes the CSF derived biomarkers (reflecting the degenerative portions of the brain), which is one of the reasons why the levels, in particular of P-tau 231 and Aβ42 in the CSF, do not appear to change as Alzheimer's Disease progresses. In actuality, the amount of released P-tau 231 and Aβ42 do increase, but the concentration of these biomarkers in CSF does not change because of the increased amounts of CSF in Alzheimer's patients. By way of a very rudimentary analogy, if one has a beaker of saltwater, one can add salt to the solution and also add a quantity of water to keep the concentration of salt in the water at the previous level. As the ventricular CSF increases, the concentration of biomarkers stays the same even though there is an increase in the quantity of neurons and their tau protein that is affected and have been broken down and are introduced to the CSF for clearance.

BRIEF DESCRIPTION OF THE DRAWINGS

FIG. 1 is a flowchart providing an overview of a first embodiment of the present invention.

FIG. 2 is a flowchart providing an overview of a second embodiment of the present invention.

DETAILED DESCRIPTION OF THE PREFERRED EMBODIMENTS

The present invention is not limited to any particular type of MRI data, as it can be a single sequence, such as high resolution fast gradient recalled echo (GRE or MPRAGE) data. This high resolution sequence for anatomical work can be acquired at the baseline and follow up in any plane (sagittal, axial or coronal). An example of this sequence is defined as TR=35 ms, TE=9 ms, 60 degree flip angle, 256×192 acquisition matrix, 1.1 mm section thickness, 124 sections, 24 cm FOV, and a 1 NEX, for a total acquisition time of 12 minutes. In addition, there can be a multi-sequence, including but not in any way limited to two IR sequences, multiple echo MR sequences, etc., that can be used to segment the brain into cerebral gray matter, white matter and cerebrospinal fluid (as known in the art, exemplified by Rusinek, H, de Leon M J, George A et al: *Alzheimer Disease: Measuring Loss of cerebral gray matter with MR Imaging*, Radiology 178: 109-114, 1991, the contents of which are herein incorporated by reference in its entirety, and Rusinek H, Chandra R: *Brain-tissue volume measurement from magnetic resonance imaging, a phantom study*, Investigative Radiology, 28: 890-895 (1993), the contents of which are herein incorporated by reference in its entirety).

As for actual measuring of ventricular volume, it has even been known in the art to be derived by CT scanning, followed by a summation of the individual section ventricular volumes, wherein the volume for each individual section is derived by a number of pixels within a user-defined cerebrospinal fluid range of attenuation coefficients.

Furthermore, for example, as disclosed by G J Harris et al., there is a user-friendly method for rapid brain and CSF volume calculation using transaxial MRI images (As disclosed in Psychiatry Research, 40(1):61-8, May 1991, the contents of which are herein incorporated by reference). In this disclosure, whole brain and CSF volumes are determined from a set of contiguous transaxial MRI images. A semi-automatic algorithm used a threshold guided edge follower, and subtraction of proton-weighted from T2-weighted images was used to highlight CSF.

In addition, as disclosed by J A Malko et al. (American Journal of Neuroradiology, 12(2):371-4, 1991 March/April, the contents of which is incorporated herein by reference) MRI imaging data was acquired using a spin-echo sequence in a single thick slice encompassing the head. In one way to scan using the MRI, which is only for illustrative purposes and not limiting to the many ways the present invention can be practiced, the diagnostic MRI sequence can be provided for by obtaining axial FSE T2-weighted images, TR=7000 and TE=100 ms, FOV=20 cm, 16 echo trains, 256×256 matrix, 1 NEX, with 48 contiguous 3 mm slices, which take approximately 3.5 minutes to complete with the present technology.

Accordingly, while persons of ordinary skill in the art have previously studied CSF volumes, heretofore, there has never been a correction for CSF biomarkers, let alone making said correction according to the ventricular size.

While the algorithms could be incorporated into many different software packages, the algorithms have been implemented herein in a MIDAS software package developed in an NYU laboratory (Tsui W-H, Rusinek H, Van Gelder P, Lebedev S: *Analyzing multi-modality Tomographic images and associated regions of interest with MIDAS*, SPIE Medical Imaging: Imaging Processing 4322, 1725034, 2001 (the contents of which are herein incorporated by reference). MIDAS is a three-dimensional image analysis package with architecture enabling the implementation of highly interactive segmentation algorithms as add-on modules, which is particularly suited for segmentation, visualization and measure of the brain.

The software application uses semi-automated procedures for (1) the volume of the CSF compartment that is known to increase with patient severity in Alzheimer's Disease, and (2) a novel method for measuring longitudinal changes in either CSF or in brain tissue. It is the increase in volume of the CSF and in particular it is known that ventricular CSF levels for tau and amyloid beta are two-fold or greater higher than lumbar CSF levels and therefore it is believed to dilute the protein level and provide inaccurate results. Also the longitudinal determinations will be of value in measuring brain pathologies and providing clinical information, biomarker information, and information regarding the effectiveness of treatment interventions.

Biomarker Dilution Factor: Semi-Automated CSF Volumes Estimated from T1-Weighted MRI Sequence The software procedure for the CSF volume computation decomposes the MR image into three regions: the brain-CSF border B, the interior region containing CSF I, and the outer brain region O. A set of edge voxels is first constructed by thresholding the image at the gray level lower than 0.55 W, where W is the average white matter signal (The constant 0.55 was determined empirically using phantom studies). The set of voxels resulting from this step are denoted as M. The interior region I is obtained as a result of a "peel" operator. I=peel(M) and the outer region O is constructed as the complement of the operator grow (M). The border region B is then constructed as:

$$B = O - I.$$

All voxels within the region I are classified as the "pure CSF". All voxels in the O region are classified as "brain tissue" voxels. Voxels within the border region B belong to the class of partially-volume tissue. These voxels may contribute to segmentation error in a simpler image processing algorithm. The Midas software automatically decomposes each element B into fractional volumes of CSF and the brain based on their gray level and algebraic formulas. If the computation of CSF volume needs to be restricted to one or more regions of interest (ROI), the sets of I, O, and B are intersected with user-specific ROIs to yield regional estimates of the CSF and brain volumes.

Semi-Automated Procedures for Collecting Longitudinal Data from MRI Scans

The main image processing steps are (1) co-registration of baseline and follow-up MR images; (2) construction of border region B and two interior regions $I_{bas}$ and $I_{fol}$, for the entire brain and for each anatomical subvolume of interest; and (3) computation of signal loss and volume loss of the brain.

The co-registration substeps (from step (1) above) include:
(a) initial alignment of baseline scan to achieve standard orientation. In one embodiment, the pathologic angle is the standard angle, but the invention is not limited to this embodiment;
(b) initial, rough co-registration by identifying three landmarks (superior colliculi, right and left optical tracts at their entry into the cranium) on baseline and follow up images. Our software determines the transformation that maps the follow up to baseline locations. No resampling is performed at this stage;
(c) exclusion of nonbrain tissues. While the intracranial structures are relatively rigid, the skin, scalp and muscles exhibit a substantial amount of plasticity. The automated software employs a region growing technique to segment out the brain parenchyma from the MR image;
(d) iteratively refining the initial transformation matrix in step (b) to minimize the cost function defined as the variance of the ratio image. The accuracy is well under the voxel size. Voxels outside the brain paremchyma are excluded from this matching process; and
(e) resampling the followup scan to match precisely the coordinate system of the baseline scan using the synch interpolation method. Both scans undergo one resampling transformation. Resampled and co-registered scans are then saved to disk.

The construction of the border region and interior region substeps (from step (2) above) include:
(a) constructing a set of brain edge voxels by thresholding the image at the level of 0.55 W, where W is the average white matter signal. (The constant 0.55 was determined empirically using phantom studies). The brain voxels resulting from this step are denoted $M_{bas}$ and $M_{fol}$;
(b) obtaining interior regions as a result of a peel operator:
(c) constructing region $O_1$ (outer border) as: grow ($M_{bas}$ union $M_{fol}$);
(d) constructing region $O_2$ (inner border) as peel ($M_{bas}$ intersection $M_{fol}$);
(e) constructing the border region B as $O_1$-$O_2$.

The stability and sensitivity of the method is due to the decomposition of each brain subvolume into the border region B and the interior regions $I_{bas}$ and $I_{fol}$. The MR signal intensity averaged over these interior regions is used to normalize the MR signal intensity across the two scans (to eliminate changes in system gain and attenuation). The border region B is a band around the brain edge over and above the shift between its location on baseline and followup scans. The border region is constructed automatically first for the entire brain, then it is intersected with brain subvolumes to yield regional borders.

The computation of the signal loss (recited in step (3) above) and volume loss of the brain is computed from the difference in MR signal in the border region of the baseline and the follow-up scans, after normalization by signal intensity in corresponding interior regions.

As the present invention assumes there is an increase in CSF volume in response to a loss (a.k.a. a reduction) in brain volume, the CSF signal change is converted to the CSF volume and the CSF volume increase and it is expressed as either the absolute volume, or the percentage of the baseline CSF volume or the percentage of the baseline intracranial volume.

In the experimental results, the highest patient baseline and follow-up classification accuracies were found with combination of the CSF corrected P-tau 231, Aβ40 and hippocampal volume measures.

Validation by Study

In a longitudinal MRI and CSF study, in a one year study of an eleven person NL control group ($X_{gds}$=1.6, plus or minus 0.5, $X_{mmse}$=29.4, plus or minus 0.7) and eight mildly cognitively impaired (MCI) patients ($X_{gds}$=3, $X_{mmse}$=28.5, plus or minus 1.2) the cross-sectional and longitudinal hippocampal and CSF volumes, and from the lumbar puncture, the CSF levels (pg/ml) of P-tau 231, Amyloid beta (AB) 1-40 (40) and AB42. The groups did not differ in age (range 52-81 years) for any of the measures.

At baseline, follow-up, and longitudinally, the MCI group was compared with the NL control group. During the study, one NL subject converted to MCI and two MCI subjects converted to Alzheimer's Disease.

The hippocampal volume was significantly reduced in the MCI group at both baseline (15%; $X_{NL}$=3.3+/31 0.35, $X_{MCI}$=2.8+/−0.26, p<0.01) and follow-up (19%; $X_{NL}$=3.2+/−0.24, $X_{MCI}$=2.6+/−0.30, p<0.001). The longitudinal hippocampal results did not reach significance. The MRI derived CSF volume did not show any cross-sectional or longitudinal changes. Significant elevations in P-tau-231 levels were found in MCI relative to controls, at both baseline (250%; $X_{NL}$=152.7+/−0.182.3, $X_{MC}$=534.7+/−451.8; t (8.7)=−2.3, p<0.05), and follow-up (710%; $X_{NL}$=69.3+/−48.5, $X_{MCI}$=561.5+/−447.2; t (8.2)=−3.3, p=0.01).

In addition, Aβ_40 was also increased at baseline (32%; $X_{NL}$=9,396.4+/−2,295.7, $X_{MCI}$=12,393.1+/−2,388.5; (t (17)=−2.8, p<0.05) and follow-up (36%; $X_{NL}$=8,564.6+/−2,174.2, $X_{MCI}$=11,643.4+/−2,809.1; (t (17)=−2.7, p<0.05). No longitudinal effects were observed for the CSF protein levels. The analyses were repeated using a logarithmic transformation of the data and observed similar results as the aforementioned. The highest baseline and follow-up patient classification accuracies (sensitivities=88% and specificities >90%, p<0.01) were found with the combination of P-tau 231, Aβ 40, and hippocampal volume. There was also a significant relationship between the hippocampal volumes and P-tau 231 level at baseline (r=−0.48, p<0.05) and at follow up (r=−0.59, p<0.01).

Correcting the CSF P-tau 23.1 level for the ventricular volume produces the only significant longitudinal effect ((t) 17)=−2.6, p<0.05). The longitudinal increase in the corrected P-tau 231 data correctly classified 74% of the total sample with an odds ratio=2.1, (p<0.01). The foregoing data and findings are set forth in de Leon, M. J., et als., *Longitudinal cerebrospinal fluid tau load increases in mild cognitive*

*impairment*, (2002) Neuroscience Letters, 333:183-186, and this reference is incorporated herein by reference in its entirety.

It should be understood by persons of ordinary skill in the art that various modifications may be made to the presently claimed invention that would lie within the spirit of the invention and the scope of the appended claims. For example, biomarkers other then the Tau and amyloid beta peptides can be tested for in the CSF. There are many brain derived substances that can be found in CSF, and the claimed invention is a useful way to properly calculate their concentration.

While the diagnosis of and study of Alzheimer's Disease is of particular interest, many other types of brain impairment/disease can be tested for. The present invention provides, inter alia, a valuable diagnostic tool to check the progression of persons as time passes. The scans from the MRI can be stored in a database, that can be attached locally, over the Internet, on a writable CD, electronically stored, etc, as desired. Furthermore, the present invention also contemplates a system for testing, the system can be a unix workstation, personal computer, midframe computer, etc. The algorithm, which can be part of the MIDAS program, can also be adapted to run on any operating system to fit need. The type of MRI machines used are also according to need.

Finally, it should also be understood that often psychometric/psychiatric and neurologic evaluations are made in conjunction with the corrected biomarker factor to increase the accuracy of the diagnosis. The algorithm may provide a factor that can be multiplied against the initial CSF biomarker concentration level, or the algorithm may alternatively provide the corrected score. Either provision of the correction factor and/or the score is clearly within the spirit of the invention and the scope of the appended claims.

What is claimed is:

1. A method for providing a cerebrospinal fluid (CSF) correction factor for CSF obtained from a patient suffering from a disease selected from the group consisting of Alzheimer's Disease and Mild Cognitive Impairment (MCI) for at least one biomarker selected from the group consisting of a Tau protein and an amyloid beta (Aβ), comprising the steps of:
   (a) measuring levels of said at least one biomarker in samples of CSF obtained from the patient;
   (b) providing semi-automated measurements of the ventricular system using quantitative anatomical protocols;
   (c) correcting the concentration dilution level in the CSF of said at least one biomarker measured in step a) by using a computer algorithm that analyzes volume and longitudinal changes in CSF measurements obtained in step (b); and
   (d) providing the CSF correction factor for level of concentration of said at least one biomarker due to increased ventricular volume of CSF caused by an increase in ventricular size.

2. The method according to claim 1, wherein the Tau protein is P-tau$_{231}$.

3. The method according to claim 1, wherein the amyloid beta is Aβ$_{42}$.

4. The method according to claim 1, wherein the amyloid beta is Aβ$_{40}$.

5. A method for providing a cerebrospinal fluid (CSF) correction factor for CSF obtained from a patient suffering from Alzheimer's Disease or Mild Cognitive Impairment (MCI) for at least one biomarker selected from the group consisting of a Tau protein and an amyloid beta (Aβ) peptide, comprising the steps of:
   (a) measuring levels of biotmarkers in CSF samples obtained from the patient;
   (b) providing semi-automated measurements of the ventricular system using quantitative anatomical protocols; and
   (c) correcting the concentration dilution level in the CSF of said at least one biomarker tested for in step (a) by a using a computer algorithm that analyzes the volume and longitudinal changes in CSF measurements obtained in step (b);and
   (d) providing the CSF correction factor for the concentration of said at least one biomarker due to increased ventricular volume of CSF.

6. The method according to claim 5, wherein the Tau protein is P-tau$_{231}$.

7. The method according to claim 5, wherein the amyloid beta is Aβ$_{42}$.

8. The method according to claim 5, wherein the amyloid beta is Aβ$_{40}$.

9. A method for providing a cerebrospinal fluid (CSF) correction factor for CSF obtained from a patient suffering from Alzheimer's Disease or Mild Cognitive Impairment (MCI), comprising the steps of:
   (a) measuring the ventricular system of the brain by scans;
   (b) measuring levels of a biomarker selected from the group consisting of a Tau protein and an amyloid beta (Aβ) peptide in CSF that has been extracted within a predetermined amount of time before or after the scanning in step (a);
   (c) correcting a concentration dilution level in the CSF of said at least one biomarker tested for in step (b) by using a computer algorithm that compares the measurements from the scans in step (a) with average values for a particular head size to determine ventricular size; and
   (d) providing the cerebrospinal fluid (CSF) correction factor for CSF obtained from a patient suffering from a neurological disease.

10. The method according to claim 9, wherein the Tau protein is P-tau$_{231}$.

11. The method according to claim 9, wherein the amyloid beta is Aβ$_{42}$.

12. The method according to claim 9, wherein the amyloid beta is Aβ$_{40}$.

13. A method for providing a correcting factor for at least one biomarker selected from the group consisting of a Tau protein and an amyloid beta (Aβ) peptide in cerebrospinal fluid (CSF) obtained from a patient suffering from Alzheimer's Disease or Mild Cognitive Impairment (MCI), comprising the steps of:
   (a) collecting longitudinal data of scans;
   (b) co-registering a baseline scan and a follow-up scan of images;
   (c) constructing a border region B and two interior regions $I_{bas}$, $I_{fol}$ for the entire brain and for each predetermined anatomical subvolume of interest;
   (d) computing signal loss and volume loss of the brain to derive a volume of CSF in the brain, and
   (e) providing an output of a correction factor for correcting a tested level of at least one biomarker in the CSF.

* * * * *